United States Patent
Tran et al.

(10) Patent No.: US 12,005,037 B2
(45) Date of Patent: Jun. 11, 2024

(54) FORMULATIONS CONTAINING EXPECTORANTS OR DECONGESTANTS

(71) Applicant: PuraCap Pharmaceutical LLC, Iselin, NJ (US)

(72) Inventors: Minh Tran, Secaucus, NJ (US); Yi Zeng, Hillsborough, NJ (US); Zhang Julia Zhang, Scotch Plains, NJ (US); Hengsheng Feng, Moorestown, NJ (US); Dahai Guo, Belle Mead, NJ (US)

( * ) Notice: Subject to any disclaimer, the term of this patent is extended or adjusted under 35 U.S.C. 154(b) by 0 days.

(21) Appl. No.: 17/933,262

(22) Filed: Sep. 19, 2022

(65) Prior Publication Data
US 2023/0017466 A1    Jan. 19, 2023

Related U.S. Application Data

(63) Continuation of application No. 16/498,199, filed as application No. PCT/US2018/023774 on Mar. 22, 2018, now abandoned.

(60) Provisional application No. 62/476,998, filed on Mar. 27, 2017.

(51) Int. Cl.
| | |
|---|---|
| A61K 31/167 | (2006.01) |
| A61K 9/48 | (2006.01) |
| A61K 31/09 | (2006.01) |
| A61K 31/137 | (2006.01) |
| A61K 31/138 | (2006.01) |
| A61K 31/485 | (2006.01) |

(52) U.S. Cl.
CPC .......... *A61K 31/167* (2013.01); *A61K 9/4825* (2013.01); *A61K 9/4858* (2013.01); *A61K 9/4866* (2013.01); *A61K 31/09* (2013.01); *A61K 31/137* (2013.01); *A61K 31/138* (2013.01); *A61K 31/485* (2013.01)

(58) Field of Classification Search
CPC .. A61K 31/167; A61K 9/4825; A61K 9/4858; A61K 9/4866; A61K 31/09; A61K 31/137; A61K 31/138; A61K 31/485
See application file for complete search history.

(56) References Cited

U.S. PATENT DOCUMENTS

| | | |
|---|---|---|
| 5,510,389 A | 4/1996 | Dhabhar |
| 9,308,166 B2 | 4/2016 | Agisim et al. |
| 9,744,133 B2 | 8/2017 | Agisim et al. |
| 2007/0249727 A1 | 10/2007 | Martin et al. |
| 2014/0243364 A1 | 8/2014 | Agisim et al. |

FOREIGN PATENT DOCUMENTS

WO    2017058836 A1    4/2017

*Primary Examiner* — Robert A Wax
*Assistant Examiner* — Olga V. Tcherkasskaya
(74) *Attorney, Agent, or Firm* — Fox Rothschild LLP (57) ABSTRACT

The present invention relates to bioavailable fill compositions containing one or more of a decongestant, an expectorant, an antitussive, an analgesic, and/or an antihistamine; capsules filled with the bioavailable fill compositions; and methods of making same.

6 Claims, 3 Drawing Sheets

FORMULATIONS CONTAINING EXPECTORANTS OR DECONGESTANTS

CROSS REFERENCE TO RELATED APPLICATION

This application is a continuation of U.S. patent application Ser. No. 16/498,199 filed on Sep. 16, 2019, which is the U.S. national phase of International Patent Application No. PCT/US18/23774 filed on Mar. 22, 2018, which claims priority to U.S. Provisional Application No. 62/476,998 filed on Mar. 27, 2017. The contents of the applications are incorporated herein by reference in their entirety.

FIELD OF THE INVENTION

This invention relates to bioavailable fill compositions containing one or more of a decongestant, an expectorant, an antitussive, an analgesic, and/or an antihistamine; capsules filled with the bioavailable fill compositions; and methods of making same.

BACKGROUND OF THE INVENTION

Combinations of various medications are frequently taken by patients suffering from colds or other viral or bacterial infections, especially respiratory infections. Combination medicines in a unitary formulation are sought for their convenience. For example, a highly concentrated solution of the medications allows the entire combination to be encapsulated in a reasonable small sized (0.2-1.8 mL) clear softgel capsule for easy swallowing. It also enhances the bioavailability of the medications. However, some medications such as acetaminophen, tend to recrystallize in such a solution. There is a need for clear, highly concentrated formulations suitable for encapsulation in capsules, such as softgel capsules, and related preparation methods.

SUMMARY OF INVENTION

This invention relates to a new formulation providing desirable combinations of active ingredients, particularly a combination of two or more of decongestant, expectorant, antitussive, analgesic, and/or antihistamine in a unitary formulation. This formulation provides convenience to a patient and aids compliance in taking the medications. The formulation can be free of any ionizing agent; namely, a compound or agent (such as alkali metal ions, i.e., lithium, sodium, potassium, rubidium, and cesium cations) capable of ionizing an active ingredient (e.g., acetaminophen here) in a solution.

An overall approach to formulating the combination of the active ingredients (AIs) is to prepare a fill composition and encapsulate it with a capsule, such as a soft gelatin capsule (softgel), specifically solubilizing the AIs in a suitable matrix comprising a polymeric solubilizing agent and water in an alkylene glycol and poly(alkylene glycol) vehicle.

In one aspect, the invention features a clear bioavailable liquid composition (e.g., softgel or hard shell fill composition) comprising: (a) two or more active ingredients selected from the group consisting of: acetaminophen, guaifenesin, phenylephrine and/or a pharmaceutically acceptable salt thereof, dextromethorphan and/or a pharmaceutically acceptable salt thereof, diphenhydramine and/or a pharmaceutically acceptable salt thereof, and pseudoephedrine and/or a pharmaceutically acceptable salt thereof; (b) a matrix comprising: 20-70 wt % (e.g., 30-70, 40-60, 45-60, 45-57%, or 46-56%) of a pharmaceutically acceptable poly(alkylene glycol) (e.g., PEG 400 or PEG 600), and 0.5-8 wt % (e.g., 1-7, 1-6, 1.5-5, 1.5-4.5, 1.9-4.1%) of a pharmaceutically acceptable alkylene glycol; and (c) a solubilizing agent comprising: 1-30 wt % (e.g., 1-25, 2-20, 3-20, 4-20, or 5-18%) of a pharmaceutically acceptable polymeric solubilizing agent (e.g., Povidone) and 1-10 wt % (e.g., 2-10, 3-10, 5-10, 5.0-9.5, or 6.0-9.5%) by weight water. The wt % values are based on the total weight of the composition, and wherein said fill composition is clear.

In one example, the matrix comprises 45-57 wt % of a pharmaceutically acceptable poly(alkylene glycol), and 1.5-4.5 wt % of a pharmaceutically acceptable alkylene glycol. In another, the matrix comprises 46-56 wt % of a pharmaceutically acceptable poly(alkylene glycol), and 1.9-4.1 wt % of a pharmaceutically acceptable alkylene glycol.

In one example, the solubilizing agent comprises 4-20 wt % of a pharmaceutically acceptable polymeric solubilizing agent, and 5-9.5 wt % by weight water. In another, the solubilizing agent comprises 5-18 wt % of a pharmaceutically acceptable polymeric solubilizing agent, and 6.0-9.5 wt % by weight water.

In some embodiments, the clear bioavailable liquid composition comprise:
  0 to about 30.0 wt % (e.g., 20-28, 21-27, 22-25, or 22.5-26.5%) acetaminophen,
  0 to about 25.0 wt % (e.g., 10-25, 14-24, or 14-23.5%) guaifenesin,
  0 to about 1.0 wt % (e.g., 0.1-0.9, 0.2-0.7, 0.5-0.7, or 0.3-0.6%) phenylephrine HCl.
  0 to about 2.0 wt % (e.g., 0.5-1.5, 1.0-1.30, or 1.10-1.25%) dextromethorphan HBr,
  0 to about 3.0 wt % (e.g., 1.0-3.0, 1.5-2.5, or 1.9-2.1%) diphenhydramine HCl, or
  0 to about 5.0 wt % (e.g., or 1.0-4.0, 2.0-4.0, or 3.0-3.5%) pseudoephedrine HCl.

In one embodiment, the clear bioavailable liquid composition comprises the following as the only active ingredients: about 22.0 to about 25.0 wt % (e.g., about 23-24, 23.0-23.5, or 23.26%) guaifenesin and about 0.5 to 0.7 wt % (e.g., about 0.55-0.65, 0.57-0.63, or 0.60%) phenylephrine HCl. For example, the clear bioavailable liquid composition can be about 860 mg comprising about 200 mg guaifenesin and about 5.13 mg phenylephrine HCl. The composition can further comprise about 404.87 mg polyethylene glycol 400, about 20 mg propylene glycol, about 150 mg Povidone (k12), and about 80 mg water.

In one embodiment, the clear bioavailable liquid composition comprises the following as the only active ingredients: about 22.0 to about 25.0 wt % (e.g., about 23-24, 23.0-23.5, or 23.12%) guaifenesin and about 1.0 to 2.0 wt % (e.g., about 1.0-1.8, 1.1-1.5, or 1.22%) dextromethorphan HBr (95%). For example, the clear bioavailable liquid composition can be about 865 mg comprising about 200 mg guaifenesin and about 10.526 mg dextromethorphan HBr (95%). The composition can further comprise about 404.474 mg polyethylene glycol 400, about 20 mg propylene glycol, about 150 mg Povidone (k12), and about 80 mg water.

In one embodiment, the clear bioavailable liquid composition comprises the following as the only active ingredients: about 21.0 to about 24.0 wt % guaifenesin (e.g., about 22-23, 22.5-23.0, or 22.6%), about 0.40 to about 1.0 wt % (e.g., about 0.4-0.6, 0.5-0.6, or 0.59%) phenylephrine HCl, and about 1.0 to 2.0 wt % (e.g., about 1.10-1.50, 1.10-1.20, or 1.19%) dextromethorphan HBr (95%). For example, the clear bioavailable liquid composition can be about 885 mg comprising about 200 mg guaifenesin, about 5.25 mg phenylephrine HCl, and about 10.526 mg dextromethorphan HBr (95%). The composition can further comprise about 419.224 mg polyethylene glycol 400, about 20 mg propylene glycol, about 150 mg Povidone (k12), and about 80 mg water.

In one embodiment, the clear bioavailable liquid composition comprises the following as the only active ingredients: 21.0 to about 24.0 wt % (e.g., about 22-23, 22.5-23.0, or 22.97%) acetaminophen, 13.0 to about 16.0 wt % (e.g., about 14-15, 14.0-14.5, or 14.13%) guaifenesin, and 0.2 to about 0.6 wt % (e.g., about 0.3-0.5, 0.35-0.4, or 0.37%) phenylephrine HCl. For example, the clear bioavailable liquid composition can be 1415 mg comprising about 325 mg acetaminophen, about 200 mg guaifenesin and about 5.25 mg phenylephrine HCl The composition can further comprise about 671.75 mg polyethylene glycol 400, about 28 mg propylene glycol, about 100 mg Povidone (k12), and about 85 mg water.

In one embodiment, the clear bioavailable liquid composition comprises the following as the only active ingredients: 25.0 to about 28.0 wt % (e.g., about 26-27, 26.0-26.5, or 26.21%) acetaminophen, 0.30 to about 0.60 wt % (e.g., about 0.4-0.5, 0.40-0.45, or 0.42%) phenylephrine HCl, and 1.0 to about 3.0 wt % (e.g., about 1.5-2.5, 2.0-2.5, or 2.02%) diphenhydramine HCl. For example, the clear bioavailable liquid composition can be about 1240 mg comprising about 325 mg acetaminophen, about 5.25 mg phenylephrine HCl and about 25 mg diphenhydramine HCl. The composition can further comprise about 684.75 mg polyethylene glycol 400, about 50 mg propylene glycol, about 65 mg Povidone (k30), and about 85 mg water.

In yet another embodiment, the clear bioavailable liquid composition comprises the following as the only active ingredients: about 21.0 to about 25.0 wt % (e.g., about 21-24, 22-24, or 22.5-23.0%) guaifenesin and about 2 to 5 wt % (e.g., about 2-4, 3-4 or 3.20-3.60%) pseudoephedrine HCl. For example, the clear bioavailable liquid composition can be about 850-890 mg comprising about 200 mg guaifenesin and about 30 mg pseudoephedrine HCl.

The above described clear bioavailable liquid composition comprises only two or three active ingredients selected from the group. The two or three active ingredients are the only active ingredients.

In another aspect, the invention provides a pharmaceutical composition in the form of a capsule (e.g., a soft gelatin capsule or a hard shell capsule) of a size suitable (e.g., 0.2-1.8 mL, 0.3-1.5, or 0.5-1.0 ml) for easy swallowing and typically containing from about 100 mg to about 2000 mg of a solubilized pharmaceutical active composition, comprising: (a) an outer shell (e.g., gelatin shell); and (b) a safe and effective mount of the clear bioavailable liquid composition described above, which is encapsulated by said outer shell.

Another aspect of the invention is directed to a softgel capsule comprising a soft gelatin capsule filled with the bioavailable liquid softgel fill composition disclosed above. In one embodiment the gelatin of said soft gelatin (softgel) capsule comprises bovine-, avian-, porcine-, marine- or vegetable-based gelatin, or a mixture of two or more thereof. In one embodiment, the softgel capsule further comprises an enteric coating. The enteric coating preferably comprises a controlled release or delayed release polymer. In one embodiment the controlled release polymer is an acid-resistant polymer.

Another aspect of the invention is directed to a bioavailable liquid fill composition consisting essentially of or consisting of the components described above.

The details of one or more embodiments of the invention are set forth in the description below. Other features, objectives, and advantages of the invention will be apparent from the description and from the claims.

DETAILED DESCRIPTION OF THE INVENTION

This invention provides a clear, liquid pharmaceutical formulation that contains a combination two or more of a decongestant, an expectorant, an antitussive, an analgesic, and/or an antihistamine. It was unexpected that the formulation can be prepared in a small size suitable for easy swallowing as a clear liquid and remain clear without recrystallization for an extended period of time (8 days up to 2 years) despite the highly concentrated active ingredients (such as two or more of acetaminophen, guaifenesin, phenylephrine, dextromethorphan, diphenhydramine, and pseudoephedrine). The formulation is suitable for preparing various oral dosage forms, e.g., soft gel capsule, suspension, solution, syrup, two-piece hard shell capsule, and nasal/oral spray. See Modern Pharmaceutics, Volume 121(2004), edited by Gilbert S. Banker and Christopher T. Rhodes, and references cited therein. See also U.S. Pat. Nos. 8,518,438, and 8,969,416, and International Patent Application No. PCT/US16/54052. These documents are hereby incorporated by reference in their entirety.

In particular, it may be used to prepare capsules (e.g., soft gels) containing a high dose of the combination in a stable solution. In that case, an overall approach to formulating the combination of the active ingredients (AIs) is to prepare a fill composition and encapsulate it with a capsule, such as a soft gelatin capsule, specifically solubilizing the AIs in a suitable matrix comprising a polymeric solubilizing agent and water in an alkylene glycol and poly(alkylene glycol) vehicle.

The solubilizing matrix can comprise two parts. Part A is a hydrophilic mixture of a pharmaceutically acceptable alkylene glycol, such as propylene glycol and a pharmaceutically acceptable poly(alkylene glycol), such as a polyethylene glycol (PEG). Part B is a mixture of a pharmaceutically acceptable solubilizing polymer, such as a polyvinylpyrrolidone (povidone) and water. Parts A and B are combined to form the solubilizing matrix, and the active ingredients are added to this solubilizing matrix to form the fill composition as clear solutions. The fill composition of the invention can then be encapsulated into capsules of the invention.

In one embodiment the pharmaceutically acceptable poly(alkylene glycol) is selected from the group consisting of poly(ethylene glycol)s (PEGs); preferably the PEGs are selected from the group consisting of PEG 200, 300, 400, 600, mixtures thereof, and mixtures of these with PEG 800, 1000, 2000, 3000, 4000, 5000, 6000, 7000, or 8000. In one embodiment the pharmaceutically acceptable alkylene glycol is propylene glycol. In one embodiment of the fill composition, the pharmaceutically acceptable polymeric solubilizing agent is a polyvinylpyrrolidone (PVP). In one embodiment the PVP is selected from the group consisting of PVP K12, PVP K17, PVP K30, PVP K60, and PVP K90; preferably the polyvinylpyrrolidone is PVP 12, PVP 17 or PVP 30.

As used herein, the term "analgesic" designates any of a number of well-known drugs which are commonly used to relieve headaches and to reduce fever. Such drugs include aspirin, acetaminophen, ibuprofen, and naproxen, among others. For the present application a preferred analgesic is acetaminophen.

The term "clear" as used herein with regard to the inventive fill compositions, means transparent, without any cloudiness or precipitation.

The term "ionizing agent" herein refers to a compound that can react with acetaminophen in the solvent system to form acetaminophen ions. Examples of an ionizing agent include both organic and inorganic bases capable of accepting hydrogen ions or donating electron pairs. Alkali or alkaline-earth metal salts or hydroxides are commonly used ionizing agents to increase the solubility of acetaminophen.

An ionizing agent can be added to the formulation to boost the solubility of acetaminophen in the solvent system. However, it can undesirably accelerate the degradation of acetaminophen. Thus, an acetaminophen formulation having an ionizing agent might be less stable. Based on the required shelf life of a formulation, a person skilled in the art can easily decide whether or not to include an ionizing agent in the formulation. In the formulation of this invention that does not include an ionizing agent, acetaminophen is dissolved at an unexpectedly high concentration in the solvent system, which, as pointed out above, contains polyvinylpyrrolidone, polyethylene glycol, and water.

The term "dissolving" herein means "evenly dispersing an active ingredient (e.g., acetaminophen, guaifenesin, phenylephrine, dextromethorphan, diphenhydramine, and pseudoephedrinea) as molecules in the solvent system containing polyvinylpyrrolidone, polyethylene glycol, and water for at least three days, as judged by the naked eye or by a magnifying optical device based on two criteria: (i) transparence of the solution, and (ii) no formation of solid precipitation.

The transitional phrase "consisting essentially of" or "consists essentially of" as used herein limits the scope of a claim to the specified materials or steps and those that do not materially affect the basic and novel characteristics of the claimed invention.

Other Components

Other components which can be incorporated into the liquid pharmaceutical core compositions of the instant invention include colorings, flavorings, preservatives, lubricants, flow-enhancers, filling aids, anti-oxidants, essences, and other aesthetically pleasing components. For example, the compositions can further contain an anti-oxidant. In some embodiments the anti-oxidant is selected from the group consisting of Butylated hydroxyanisole (BHA), Butylated hydroxytoluene (BHT), and mixtures thereof.

Process of Making

Figure 2:
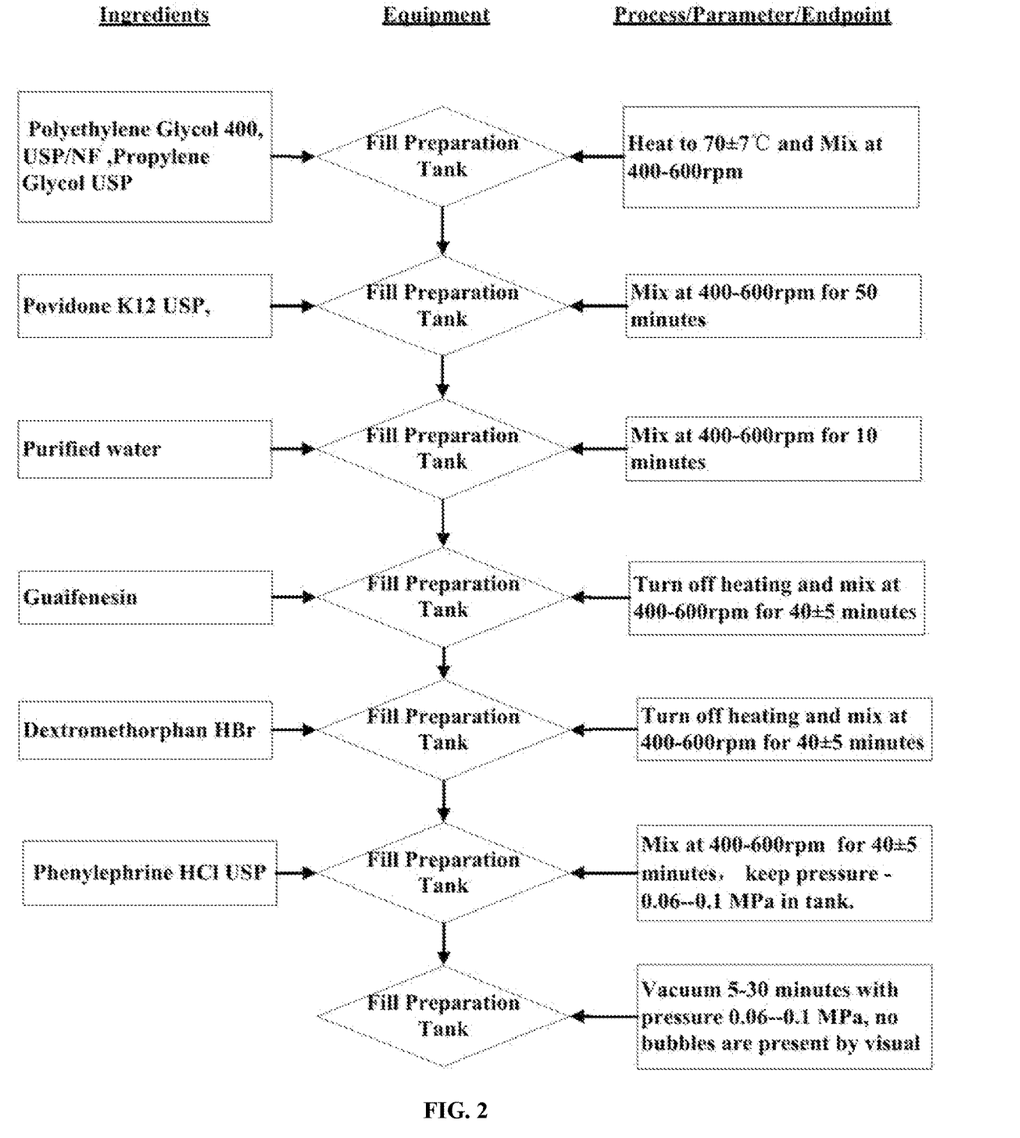
FIG. 2 is a chart showing an exemplary process flow for a fill preparation.

Another aspect of the invention is directed to a method of preparing a clear liquid softgel fill composition as disclosed above, e.g., that shown in FIG. 2. In one example, the method comprises: (a) stirring polyethylene glycol or a mixture of polyethylene glycols, and propylene glycol with heating to 70° C.±10° C. (e.g., 70° C.±7° C.) until a clear solution is obtained; (b) slowly adding polyvinylpyrrolidone in small quantities with continuous mixing and heating to 70° C.±10° C. (e.g., 70° C.±7° C.), until a clear solution is obtained; (c) adding purified water with continuous mixing and heating to 70° C.±10° C. (e.g., 70° C.±7° C.), until a clear solution is obtained; (d) adding a first active ingredient (e.g., guaifenesin) with continuous mixing and heating to 70° C.±10° C. (e.g., 70° C.±7° C.), until a clear solution is obtained; In some examples, once guaifenesin is added, the heat is turned off but the solution is still warm. (e) adding a second active ingredient (e.g., dextromethorphan HBr) with continuous mixing and optionally heating to, e.g., 70° C.±10° C. (e.g., 70° C.±7° C.), until a clear solution is obtained; (f) successively adding a third active ingredient (e.g., phenylephrine HCl) with continuous mixing and optionally heating up to 80° C., until a clear solution is obtained; and (g) cooling to ambient temperature and deaerating the clear liquid softgel fill solution. In some embodiment of the method the polyethylene glycol is selected from the group consisting of PEG 400, PEG 600 and mixtures thereof. In some embodiments of the method the temperature of the solution during the addition of dextromethorphan HBr is up to 55° C., and the temperature of the solution during the addition of phenylephrine HCl is below 35° C.

The liquid softgel fill formulation can be encapsulated in soft gelatin shells to form softgel capsules, for example by using a conventional rotary die process. Suitable soft gelatin shells may include (i) gelatin, 20-60% by weight; (ii) glycerin, 0-30% by weight; (iii) sorbitol, 0-30% by weight; (iv) purified water, 20-50% by weight; and (v) artificial color, 0.0001-0.002% by weight. The highly concentrated solution of active ingredients found in the liquid softgel fill formulations of the present invention allows the entire combination to be encapsulated into a reasonably small sized (0.2-1.8 mL) clear softgel capsule for easy swallowing. The inventive formulation also enhances the bioavailability of the active ingredients. Further, encapsulation of the ingredients masks the negative taste of the active ingredients so that compliance issues with taking the medication are minimized.

The softgel capsules of the invention can also be prepared by other methods well known in the art. See e.g., P. K. Wilkinson et al., "Softgels: Manufacturing Considerations," Drugs and the Pharmaceutical Sciences, 41 (Specialized Drug Delivery Systems); P. Tyle, Ed. (Marcel Dekker, Inc., New York, 1990) 409-449; F. S. Hom et al., "Capsules, Soft" Encyclopedia of Pharmaceutical Technology, vol. 2; J. Swarbrick and J. C. Boylan, eds. (Marcel Dekker, Inc., New York, 1990) pp. 269-284; M. S. Patel et al., "Advances in Softgel Formulation Technology," Manufacturing Chemist, vol. 60, no. 7, pp. 26-28 (July 1989); M. S. Patel et al., "Softgel Technology," Manufacturing Chemist, vol. 60, no. 8, pp. 47-49 (August 1989); R. F. Emerson, "Softgel (Soft Gelatin Capsule) Update," Drug Development and Industrial Pharmacy (Interphex '86 Conference), vol. 12, no. 8 & 9, pp. 1133-1144 (1986); and W. R. Ebert, "Soft Elastic Gelatin Capsules: A Unique Dosage Form," Pharmaceutical Technology, vol. 1, no. 5, pp. 44-50 (1977).

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18 to 22. Other meanings of "about" may be apparent from the context, such as rounding off, so, for example "about 1" may also mean from 0.5 to 1.4.

Polyvinylpyrrolidone, also known as Polyvidone or Povidone, is a water-soluble polymer. Polyvinylpyrrolidone used in this invention has an molecular weight in the range of 2,000 to 1,500,000 Dalton, e.g., 2,000 to 62,000 Dalton, 2,000 to 4,000 Dalton, 4,000 to 18,000 Dalton, or 6,000 to 15,000 Dalton. Polyvinylpyrrolidone products are commonly graded by K values. The K value is an index for correlating relative viscosity with the average degree of polymerization. See Cellulose Chem. 1932, 13, 60. The K value is calculated by the following formula:

$$K=(1.5 \log \eta_{rel}-1)/(0.15+0.003c)+(300c \log \eta_{rel}+(c+1.5c \log \eta_{rel})^2)^{1/2}/(0.1c+0.003c^2)$$

$\eta_{rel}$: Relative viscosity of aqueous polyvinylpyrrolidone solution to water. c: Content of polyvinylpyrrolidone in an aqueous polyvinylpyrrolidone solution (w 4%).

Polyvinylpyrrolidone used in the formulation has a K value of 12 to 90, e.g., 12, 15, 17, 25, or 30. Polyvinylpyrrolidone is designated as Povidone in the United States Pharmacopeial Convention ("USP"). Polyvinylpyrrolidone products are commercially available and generally include K values in their trade names, e.g., Polyvinylpyrrolidone K17 or Povidone K17. There are correlations between K values and molecular weights. For example, polyvinylpyrrolidone K12 has a molecular weight of 2,000 to 4,000 Dalton, K15 6,000 to 15,000 Dalton, K17 4,000 to 18,000 Dalton, K30 40,000 to 62,000 Dalton, and K90 1,000,000 to 1,500,000 Dalton. Polyvinylpyrrolidone products from different vendors may have different average molecular weights, which typically fall into the ranges cited above.

Polyvinylpyrrolidone herein refers to a single product or a mixture of several products. For example, it can be polyvinylpyrrolidone K12, K15, K17, K25, K30, K60, K90, or a mixture thereof. Polyvinylpyrrolidone enhances the solubility of AIs in the solvent system containing polyvinylpyrrolidone, polyethylene glycol, water, and optionally propylene glycol or other components.

Polyethylene glycol, also known as "PEG," has a formula of $H(OCH_2CH_2)_nOH$, wherein n is 4 or greater. A number generally follows the name PEG to indicate its average molecular weight. For example, PEG-400 has an average molecular weight of about 400 Dalton. See Cosmetic Ingredient Dictionary, 3d Ed. (1982), pages 201-03; Merck Index, 10th Ed. (1983), page 1092.

Polyethylene glycol used in this invention is a clear viscous liquid or a white solid at room temperature, and can be dissolved in water and many organic solvents. Its molecular weight can be between 200 Dalton and 800 Dalton, preferably 400-600 Dalton. The solvent system can contain a single polyethylene glycol product or a mixture of two or more polyethylene glycol products.

The term "pharmaceutically acceptable salts" refers to salts prepared from pharmaceutically acceptable non-toxic bases including inorganic bases and organic bases. Salts derived from nonorganic bases include sodium, potassium, lithium, ammonia, calcium, magnesium, ferrous, zinc, manganous, aluminum, ferric, manganic salts and the like. Salts derived from pharmaceutically acceptable organic non-toxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, oholine, betaine, ethylenediamine, glucosamine, methylglycamine, theobromine, purines, piperazine, piperidine, polyamine resins and the like.

EXAMPLES

Example 1 Bioavailable Liquid Softgel Fill Composition Comprising Guaifenesin and Phenylephrine A soft gelatin capsule containing a concentrated bioavailable liquid fill composition was prepared from the following ingredients.

| Fill Ingredients | Formulation #1 mg/capsule | Weight % |
| --- | --- | --- |
| Polyethylene glycol 400, USP | 404.87 | 47.08% |
| Propylene Glycol, USP | 20 | 2.33% |
| Povidone (K-12) USP | 150 | 17.44% |
| Povidone (K-30) USP | 0 | 0.00% |
| Purified Water, USP | 80 | 9.30% |
| Acetaminophen, USP | 0 | 0.00% |
| Guaifenesin | 200 | 23.26% |
| Phenylephrine HCl, USP | 5.13 | 0.60% |
| Dextromethorphan HBr (95%) | 0 | 0.00% |
| Diphenhydramine HCl | 0 | 0.00% |
| Pseudoephedrine | 0 | 0.00% |
| Total | 860 | 100.00% |

The above ingredients were combined in the manner shown in FIG. 2 except no dextromethorphan HBr was added.

Figure 1:
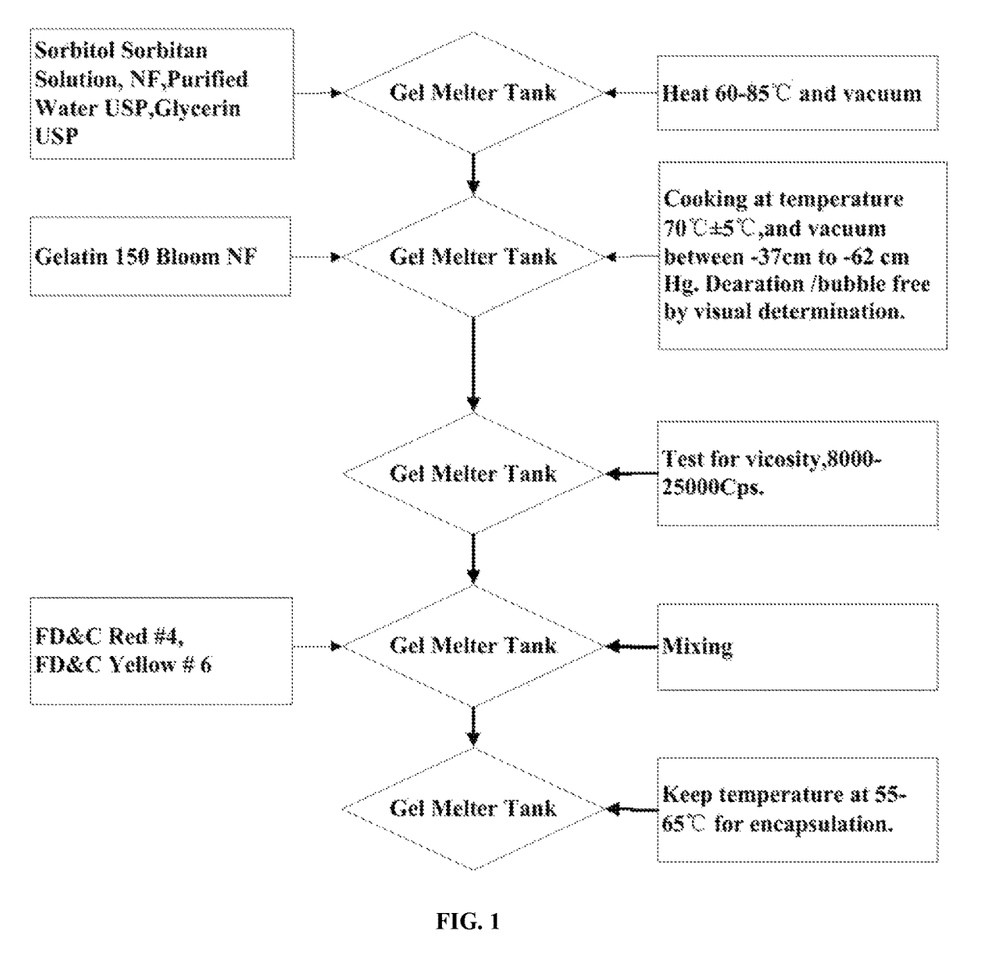
FIG. 1 is a chart showing an exemplary process flow for gel mass preparation.
Figure 3:
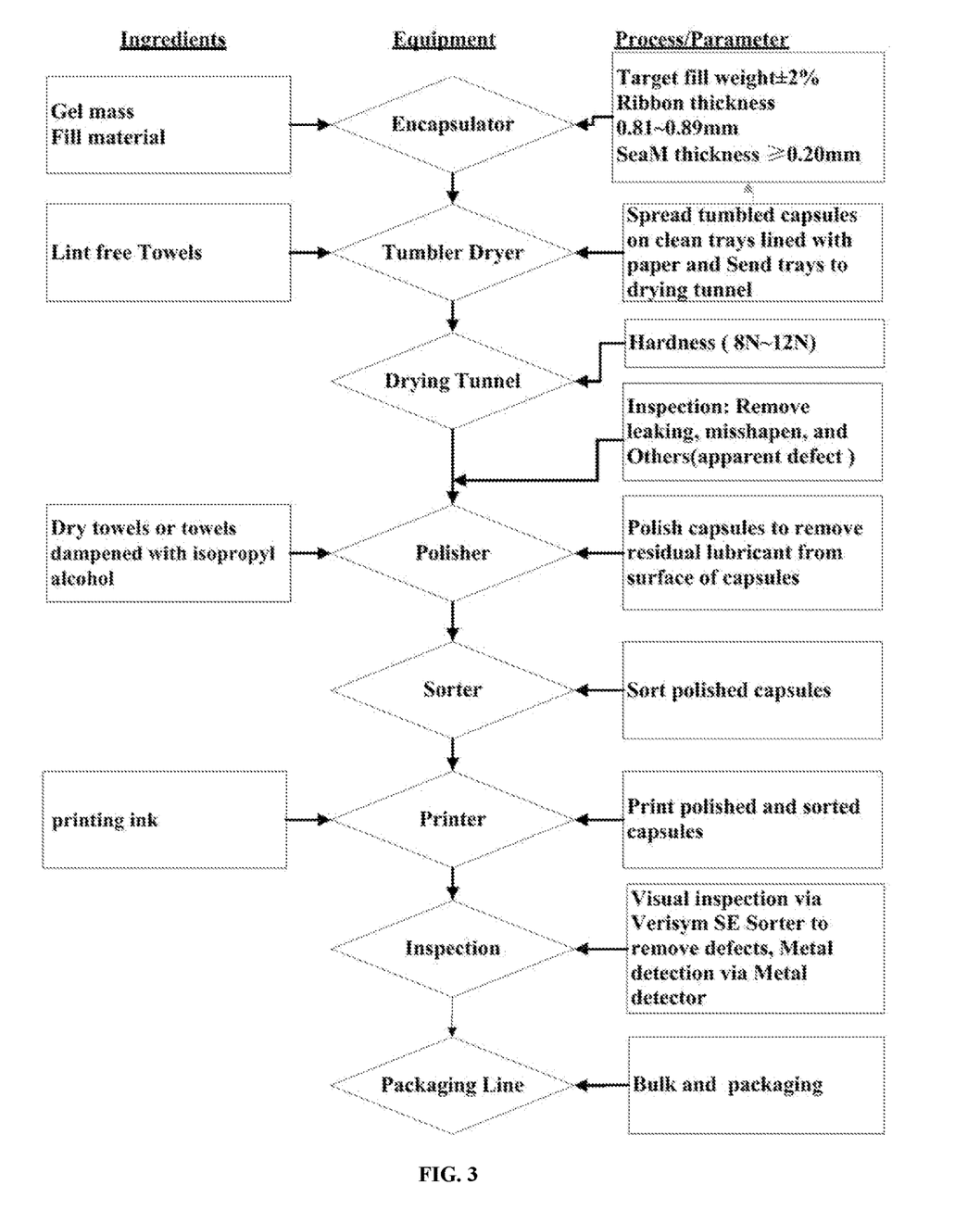
FIG. 3 is a chart of showing an exemplary process flow for encapsulation and post-process.

Soft gelatin capsules were prepared from the following gel ingredients in a manner similar to that shown in FIG. 1 except no D&C Yellow #10, FD&C Red #40, FD&C Yellow #6, D&C Red #33 or FD&C Blue #1 was added. The above formulation was then encapsulated in the soft gelatin capsule and further processed in the manner shown in FIG. 3. The resulting soft gelatin capsules are suitable for oral administration.

| Gel ingredients | |
| --- | --- |
| Gelatin 150 Bloom NF | Yes |
| Glycerin USP | Yes |
| Sorbitol Sorbitan Solution | Yes |
| D&C Yellow# 10 | — |
| FD&C Red#40 | — |
| FD&C Yellow#6 | — |
| D&C Red#33 | — |
| FD&C Blue #1 | — |
| Encapsulation | |
| lubricant | Yes, trace |
| Isopropyl Alcohol, USP | Yes, trace |
| White Ink | Yes, trace |

Example 2 Bioavailable Liquid Softgel Fill Composition Comprising Guaifenesin and Dextromethorphan A soft gelatin capsule containing a concentrated bioavailable liquid fill composition was prepared from the following ingredients.

| Fill Ingredients | Formulation #3 mg/cap | Weight % |
|---|---|---|
| Polyethylene glycol 400, USP | 404.474 | 46.76% |
| Propylene Glycol, USP | 20 | 2.31% |
| Povidone (K-12) USP | 150 | 17.34% |
| Povidone (K-30) USP | 0 | 0.00% |
| Purified Water, USP | 80 | 9.25% |
| Acetaminophen, USP | 0 | 0.00% |
| Guaifenesin | 200 | 23.12% |
| Phenylephrine HCl, USP | 0 | 0.00% |
| Dextromethorphan HBr (95%) | 10.526 | 1.22% |
| Diphenhydramine HCl | 0 | 0.00% |
| Pseudoephedrine | 0 | 0.00% |
| Total | 865 | 100.00% |

The above ingredients were combined in the manner shown in FIG. 2 except no Phenylephrine HCl was added.

Soft gelatin capsules were prepared from the following gel ingredients in a manner similar to that shown in FIG. 1 except only Yellow #6 was added. The above formulation was then encapsulated in the soft gelatin capsule and further processed in the manner shown in FIG. 3. The resulting soft gelatin capsules are suitable for oral administration.

| Gel ingredients | |
|---|---|
| Gelatin 150 Bloom NF | Yes |
| Glycerin USP | Yes |
| Sorbitol Sorbitan Solution | Yes |
| D&C Yellow# 10 | — |
| FD&C Red#40 | — |
| FD&C Yellow#6 | Yes |
| D&C Red#33 | — |
| FD&C Blue #1 | — |
| Encapsulation | |
| lubricant | Yes, trace |
| Isopropyl Alcohol, USP | Yes, trace |
| White Ink | Yes, trace |

Example 3 Bioavailable Liquid Softgel Fill Composition Comprising Guaifenesin, Phenylephrine, and Dextromethorphan A soft gelatin capsule containing a concentrated bioavailable liquid fill composition was prepared from the following ingredients.

| Fill Ingredients | Formulation #4 mg/cap | Weight % |
|---|---|---|
| Polyethylene glycol 400, USP | 419.224 | 47.37% |
| Propylene Glycol, USP | 20 | 2.26% |
| Povidone (K-12) USP | 150 | 16.95% |
| Povidone (K-30) USP | 0 | 0.00% |
| Purified Water, USP | 80 | 9.04% |
| Acetaminophen, USP | 0 | 0.00% |
| Guaifenesin | 200 | 22.60% |
| Phenylephrine HCl, USP | 5.25 | 0.59% |
| Dextromethorphan HBr (95%) | 10.526 | 1.19% |
| Diphenhydramine HCl | 0 | 0.00% |
| Pseudoephedrine | 0 | 0.00% |
| Total | 885 | 100.00% |

The above ingredients were combined in the manner shown in FIG. 2.

Soft gelatin capsules were prepared from the following gel ingredients in a manner similar to that shown in FIG. 1. The above formulation was then encapsulated in the soft gelatin capsule and further processed in the manner shown in FIG. 3. The resulting soft gelatin capsules are suitable for oral administration.

| Gel ingredients | |
|---|---|
| Gelatin 150 Bloom NF | Yes |
| Glycerin USP | Yes |
| Sorbitol Sorbitan Solution | Yes |
| D&C Yellow#10 | — |
| FD&C Red#40 | Yes |
| FD&C Yellow#6 | Yes |
| D&C Red#33 | — |
| FD&C Blue #1 | — |
| Encapsulation | |
| lubricant | Yes, trace |
| Isopropyl Alcohol, USP | Yes, trace |
| White Ink | Yes, trace |

Example 4 Bioavailable Liquid Softgel Fill Composition Comprising Acetaminophen, Guaifenesin, and Phenylephrine A soft gelatin capsule containing a concentrated bioavailable liquid fill composition was prepared from the following ingredients.

| Fill Ingredients | Formulation #5 mg/cap | Weight % |
|---|---|---|
| Polyethylene glycol 400, USP | 671.75 | 47.47% |
| Propylene Glycol, USP | 28 | 1.98% |
| Povidone (K-12) USP | 100 | 7.07% |
| Povidone (K-30) USP | 0 | 0.00% |
| Purified Water, USP | 85 | 6.01% |
| Acetaminophen, USP | 325 | 22.97% |
| Guaifenesin | 200 | 14.13% |
| Phenylephrine HCl, USP | 5.25 | 0.37% |
| Dextromethorphan HBr (95%) | 0 | 0.00% |
| Diphenhydramine HCl | 0 | 0.00% |
| Pseudoephedrine | 0 | 0.00% |
| Total | 1415 | 100.00% |

The above ingredients were combined in the manner shown in FIG. 2 except that acetaminophen was added and no dextromethorphan HBr was added.

Soft gelatin capsules were prepared from the following gel ingredients in a manner similar to that shown in FIG. 1 except that no FD&C Red #40, FD&C Yellow #6, D&C Red #33 or FD&C Blue #1 was added while D&C Yellow #10 is added. The above formulation was then encapsulated in the soft gelatin capsule and further processed in the manner shown in FIG. 3. The resulting soft gelatin capsules are suitable for oral administration.

| Gel ingredients | |
|---|---|
| Gelatin 150 Bloom NF | Yes |
| Glycerin USP | Yes |
| Sorbitol Sorbitan Solution | Yes |
| D&C Yellow#10 | Yes |
| FD&C Red#40 | — |
| FD&C Yellow#6 | — |
| D&C Red#33 | — |
| FD&C Blue #1 | — |

-continued

| Encapsulation | |
|---|---|
| lubricant | Yes, trace |
| Isopropyl Alcohol, USP | Yes, trace |
| White Ink | Yes, trace |

Example 5 Bioavailable Liquid Softgel Fill Composition Comprising Acetaminophen, Phenylephrine, and Diphenhydramine A soft gelatin capsule containing a concentrated bioavailable liquid fill composition was prepared from the following ingredients.

| Fill Ingredients | Formulation #6 mg/cap | Weight % |
|---|---|---|
| Polyethylene glycol 400, USP | 684.75 | 55.22% |
| Propylene Glycol, USP | 50 | 4.03% |
| Povidone (K-12) USP | 0 | 0.00% |
| Povidone (K-30) USP | 65 | 5.24% |
| Purified Water, USP | 85 | 6.85% |
| Acetaminophen, USP | 325 | 26.21% |
| Guaifenesin | 0 | 0.00% |
| Phenylephrine HCl, USP | 5.25 | 0.42% |
| Dextromethorphan HBr (95%) | 0 | 0.00% |
| Diphenhydramine HCl | 25 | 2.02% |
| Pseudoephedrine | 0 | |
| Total | 1240 | 100.00% |

The above ingredients were combined in the manner shown in FIG. 2 except that (i) acetaminophen and diphenhydramine HCl were added and (ii) neither guaifenesin nor dextromethorphan HBr was added.

Soft gelatin capsules were prepared from the following gel ingredients in a manner similar to that shown in FIG. 1 except that no D&C Yellow #10, FD&C Red #40, or FD&C Yellow #6 was added while D&C Red #33 and FD&C Blue #1 were added. The above formulation was then encapsulated in the soft gelatin capsule and further processed in the manner shown in FIG. 3. The resulting soft gelatin capsules are suitable for oral administration.

| Gel ingredients | |
|---|---|
| Gelatin 150 Bloom NF | Yes |
| Glycerin USP | Yes |
| Sorbitol Sorbitan Solution | Yes |
| D&C Yellow#10 | — |
| FD&C Red#40 | — |
| FD&C Yellow#6 | — |
| D&C Red#33 | Yes |
| FD&C Blue #1 | Yes |
| Encapsulation | |
| lubricant | Yes, trace |
| Isopropyl Alcohol, USP | Yes, trace |
| White Ink | Yes, trace |

Example 6 Bioavailable Liquid Softgel Fill Composition Comprising Guaifenesin and Pseudoephedrine A soft gelatin capsule containing a concentrated bioavailable liquid fill composition is prepared from the following ingredients: Guaifenesin (200 mg) and Pseudoephedrine (30 mg) per 850-890 mg per capsule. The above ingredients are combined in a manner similar to that shown in FIG. 2. Soft gelatin capsules are prepared in a manner similar to that shown in FIG. 1. The above formulation is then encapsulated in the soft gelatin capsule and further processed in the manner shown in FIG. 3. The resulting soft gelatin capsules are suitable for oral administration.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

The invention claimed is:

1. A clear bioavailable liquid composition comprising:
   (a) active ingredients selected from the group consisting of:
      (i) from 22 wt % to 25 wt % of guaifenesin and from 0.5 wt % to 0.7 wt % of phenylephrine HCl;
      (ii) from 22 wt % to 25 wt % of guaifenesin and from 1 wt % to 2 wt % of dextromethorphan HBr;
      (iii) from 21 wt % to 24 wt % of guaifenesin, from 0.4 wt % to 1 wt % of phenylephrine HCl, and from 1 wt % to 2 wt % of dextromethorphan HBr; or
      (iv) from 21 wt % to 25 wt % of guaifenesin and from 2 wt % to 5 wt % of pseudoephedrine HCl;
   (b) a matrix comprising:
      20-70 wt % of a pharmaceutically acceptable poly(alkylene glycol), and
      0.5-8 wt % of a pharmaceutically acceptable alkylene glycol; and
   (c) a polymeric solubilizing agent consisting of 1-30 wt % of polyvinylpyrrolidone; and
   (d) 1-10 wt % of water;
   wherein the wt % values are based on the total weight of the composition, and
   wherein the liquid composition remains clear without recrystallization for up to 2 years at room temperature.

2. The clear bioavailable liquid composition of claim 1, wherein 860 mg of the composition consists of:
   200 mg of guaifenesin;
   5.13 mg of phenylephrine HCl;
   404.87 mg of polyethylene glycol 400 having a molecular weight of 400 daltons,
   20 mg of propylene glycol;
   150 mg of polyvinylpyrrolidone having a molecular weight of 2,000 daltons; and
   80 mg of water.

3. The clear bioavailable liquid composition of claim 1, wherein 865 mg of the composition consists of:
   200 mg of guaifenesin,
   10.526 mg of dextromethorphan HBr,
   404.474 mg of polyethylene glycol 400 having a molecular weight of 400 daltons,
   20 mg of propylene glycol,
   150 mg of polyvinylpyrrolidone having a molecular weight of 2,000 daltons, and
   80 mg of water.

4. The clear bioavailable liquid composition of claim 1, wherein 885 mg of the composition consisting of:
   200 mg of guaifenesin,
   5.25 mg of phenylephrine HCl,
   10.526 mg of dextromethorphan HBr,
   419.224 mg of polyethylene glycol 400 having a molecular weight of 400 daltons,
   20 mg of propylene glycol,
   150 mg of polyvinylpyrrolidone having a molecular weight of 2,000 daltons, and
   80 mg of water.

5. The clear bioavailable liquid composition of claim 1, wherein 850-890 mg of the composition comprises:
   200 mg of guaifenesin and
   30 mg of pseudoephedrine HCl.

6. A pharmaceutical composition in a form of a soft gelatin capsule containing:
   (a) an outer gelatin shell; and
   (b) from 100 mg to 2,000 mg of the clear bioavailable liquid composition of claim 1 which is encapsulated by said outer gelatin shell.

\* \* \* \* \*